US007481975B2

(12) United States Patent
Read

(10) Patent No.: US 7,481,975 B2
(45) Date of Patent: Jan. 27, 2009

(54) HYDROGEN PEROXIDE INDICATOR AND METHOD

(75) Inventor: David M. Read, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 683 days.

(21) Appl. No.: 10/890,612

(22) Filed: Jul. 14, 2004

(65) Prior Publication Data

US 2004/0265170 A1 Dec. 30, 2004

Related U.S. Application Data

(63) Continuation of application No. 09/453,726, filed on Dec. 2, 1999, now Pat. No. 6,790,411.

(51) Int. Cl.
| | |
|---|---|
| A61L 9/00 | (2006.01) |
| G01N 21/00 | (2006.01) |
| G01N 31/00 | (2006.01) |
| G01N 33/00 | (2006.01) |
| G01N 21/77 | (2006.01) |
| G01J 1/48 | (2006.01) |
| A62B 7/08 | (2006.01) |
| A61B 17/06 | (2006.01) |
| B65D 85/00 | (2006.01) |
| C12Q 1/22 | (2006.01) |
| C12Q 1/02 | (2006.01) |
| C12N 11/02 | (2006.01) |

(52) U.S. Cl. .............. 422/57; 422/1; 422/4; 422/5; 422/28; 422/32; 422/34; 422/83; 422/87; 422/119; 422/123; 422/292; 422/300; 422/305; 422/306; 422/307; 436/1; 436/2; 436/135; 436/169; 206/438; 206/439; 206/459.1; 252/408.1; 435/29; 435/31; 435/177; 523/161

(58) Field of Classification Search ............... 422/1, 422/4–5, 28, 32, 34, 55, 57, 83, 86, 119, 422/123, 292, 300, 305–307; 436/1–2, 135, 436/164, 169; 206/438–439, 459.1; 252/408.1; 435/31, 29, 177; 523/161
See application file for complete search history.

(56) References Cited

U.S. PATENT DOCUMENTS

| | | | |
|---|---|---|---|
| 4,046,577 A | 9/1977 | Muzyczko et al. | |
| 4,155,895 A | 5/1979 | Rohowetz et al. | |
| 4,298,569 A * | 11/1981 | Read | 422/27 |
| 4,362,645 A * | 12/1982 | Hof et al. | 252/408.1 |
| 4,643,876 A | 2/1987 | Jacobs et al. | |
| 4,756,758 A * | 7/1988 | Lent et al. | 106/31.32 |
| 4,756,882 A | 7/1988 | Jacobs et al. | |
| 4,863,627 A | 9/1989 | Davies et al. | |
| 4,892,706 A | 1/1990 | Kralovic et al. | |
| 4,956,145 A | 9/1990 | Cummings et al. | |
| 5,053,339 A | 10/1991 | Patel | |
| 5,087,659 A | 2/1992 | Fujisawa | |
| 5,139,957 A | 8/1992 | Grack | |
| 5,352,282 A | 10/1994 | Miller | |
| 5,378,430 A * | 1/1995 | Nieves et al. | 422/57 |
| 5,445,792 A | 8/1995 | Rickloff et al. | |
| 5,482,684 A | 1/1996 | Martens et al. | |
| 5,518,927 A | 5/1996 | Malchesky et al. | |
| 5,620,656 A | 4/1997 | Wensky et al. | |
| 5,942,438 A | 8/1999 | Antonoplos et al. | |
| 5,955,025 A * | 9/1999 | Barrett | 422/28 |
| 5,990,199 A * | 11/1999 | Bealing et al. | 523/161 |
| 6,063,631 A | 5/2000 | Ignacio | |
| D433,511 S | 11/2000 | Nieves | |
| D438,980 S | 3/2001 | Hehenberger | |
| D439,344 S | 3/2001 | Hehenberger | |
| 6,218,189 B1 | 4/2001 | Antonoplos et al. | |
| 6,238,623 B1 | 5/2001 | Amhof et al. | |
| 6,267,242 B1 | 7/2001 | Nagata et al. | |
| 6,287,518 B1 | 9/2001 | Ignacio et al. | |
| 6,346,417 B1 | 2/2002 | Ignacio et al. | |
| 6,352,837 B1 | 3/2002 | Witcher et al. | |
| 6,410,338 B1 | 6/2002 | Lippold et al. | |
| 6,440,744 B1 | 8/2002 | Ignacio et al. | |
| 6,488,890 B1 | 12/2002 | Kircokf | |
| 6,551,555 B2 | 4/2003 | Antonoplos et al. | |
| 2002/0151084 A1 | 10/2002 | Lippold et al. | |

FOREIGN PATENT DOCUMENTS

| | | |
|---|---|---|
| DE | 273 775 A1 | 7/1988 |
| DE | 273776 A1 | 11/1989 |
| EP | 0 914 833 | 12/1999 |
| EP | 1052507 A2 | 11/2000 |
| EP | 1 465 671 B1 | 12/2005 |
| JP | 49-046440 | 12/1974 |
| JP | 11-178904 | 7/1999 |
| WO | WO 92/22806 | 12/1992 |
| WO | WO 96/33242 | 10/1996 |
| WO | WO 98/46279 | 10/1998 |
| WO | WO 98/46994 | 10/1998 |
| WO | WO 98/52621 | 11/1998 |
| WO | WO 98/58683 | 12/1998 |
| WO | WO 00/50634 A1 | 8/2000 |
| WO | WO 00/61200 | 10/2000 |
| WO | WO 00/73783 A1 | 12/2000 |
| WO | WO 01/40792 | 6/2001 |

OTHER PUBLICATIONS

Bishop, "Chapter 8B: Oxidation-Reduction Indicators of High Formal Potential," *Indicators*, Bishop, ed., Pergamon Press Ltd., Braunschweig, Germany, Title Page, publication page, table of contents, and pp. 531-684 (1972).

(Continued)

*Primary Examiner*—Jill Warden
*Assistant Examiner*—Monzer R. Chorbaji
(74) *Attorney, Agent, or Firm*—Dean A Ersfeld

(57) ABSTRACT

The present invention provides a hydrogen peroxide indicator that includes a substrate on which is disposed an indicator composition that includes at least one of a select group of colorants. As a result of contact with hydrogen peroxide, the colorants change color, and even become colorless, thereby providing an indication of the presence of hydrogen peroxide.

2 Claims, No Drawings

OTHER PUBLICATIONS

Lillie et al., "Ch. 2: The General Nature of Dyes and Their Classifaction," *H.J. Conn's Biological Stains, a Handbook on the Nature and Uses of the Dyes Employed in the Biological Laboratory*, 9th ed., The Williams & Wilkins Company, available from the Sigma Chemical Company, St. Louis, Mo., Title page, publication page, and pp. 19-32 (1977).

Aldrich Chemical Company Handbook of Fine Chemicals and Laboratory Equipment, 2003-2004, p. 56 with "Allylurea" listed at the top (Acid Blue #7 is listed as Alphazurine A).

Haber et al., "The Catalytic Decomposition of Hydrogen Peroxide by Iron Salts," *Proceedings of the Royal Society*, Nov. 15, 1934; vol. 14, No. 861: Title page, Publication page, Table of Contents, and pp. 332-351.

Nakagawa et al., "Characteristic Bleaching Profiles of Cyanine Dyes Depending on Active oxygen Species in the Controlled Fenton Reaction," *Biol. Pharm. Bull.*, Nov. 1993; vol. 16, No. 11: pp. 1061-1064.

*Product data sheet* (*i.e. sales or company literature*): "Alphabetical List og Products" from ICN, Biochemicals and Reagents Catalog, 2002/2003. Title page and Section A (1 pg) (listing of Alkali Blue 6B also known as acid blue 119); 2 pgs total.

*Product data sheet* (*i.e. sales or company literature*): "Manufacturer of Dyes and Color: Abbey Color in Philadelphia" datasheet [online]. Abbey Color, Philadelphia, PA, 2003 [retrieved on May 23, 2003]. Retrieved from the Internet: <URL: http://www.abbeycolor.com/cgi/dyes.product.cgi>; 1 pg (listed as p. 1 of 5).

*Product data sheet* (*i.e. sales or company literature*): "Material Safety Data Sheet" datasheet. Sigma Chemical, Co., St. Louis, MO, valid from Nov. 1999 to Jan. 2000. Catalog No. A2931. Name: Alkali Blue 6B Free Acid. 2 pgs.

Technical Data Sheet and Material Safety Data Sheet for SUNFAST Red 19, Sun Chemical Corporation, Cincinnati, OH (13 pgs total).

\* cited by examiner

HYDROGEN PEROXIDE INDICATOR AND METHOD

CROSS REFERENCE TO RELATED APPLICATIONS

This is a continuation of patent application Ser. No. 09/453,726, filed on Dec. 2, 1999, which is now allowed, hereby incorporated herein by reference.

BACKGROUND OF THE INVENTION

Medical instruments, particularly surgical instruments, are typically sterilized prior to use using steam or other sterilizing/disinfecting gases or liquids. A traditional sterilization process uses steam under pressure. Alternative sterilization processes use ethylene oxide or hydrogen peroxide in vapor form as the sterilant.

The use of hydrogen peroxide and other chemical vapor phase sterilization techniques typically involve operating temperatures well below those associated with steam sterilization. These "low temperature" technologies generally operate at temperatures below about 80° C., and often below about 65° C. For hydrogen peroxide sterilization, the sterilized goods are typically available for use shortly after the completion of the sterilization cycle. This is because the decomposition products (e.g., water and oxygen) are non-toxic. The potency of the hydrogen peroxide may be augmented by the presence of electrical energy in the form of an ionizing plasma field.

Sterilization indicators are used to monitor whether a sterilization process has been performed. Sterilization indicators typically include an indicator composition, carried on a substrate, that changes color during the sterilization process. Conventional indicators for hydrogen peroxide, however, often fade upon exposure to light. Thus, there is still a need for a suitable indicator that includes a color change composition for indicating the vapor phase sterilization of an article using hydrogen peroxide.

SUMMARY OF THE INVENTION

The present invention is directed to a method and indicator for detecting the presence of hydrogen peroxide in the vapor phase. The method and indicator are particularly well suited for monitoring whether a hydrogen peroxide sterilization process has been performed.

The present invention provides a hydrogen peroxide indicator that includes a substrate and an indicator composition disposed thereon, wherein the indicator composition includes at least one colorant selected from the group consisting of Malachite green oxalate, Crystal violet, Methyl violet 2B, Ethyl violet, New fuchsin, Victoria blue B, Victoria pure blue BO, Toluidine blue O, Luxol brilliant green BL, Disperse blue 1, Brilliant blue R, Victoria blue R, Quinea green B, Thionin, Meldolas blue, Methylene green, Lissamine green B, Alkali blue 6B, Brilliant green, Spirit soluble HLK BASF, Victoria green S extra, Acid violet 17, Eriochrome black T, Eriochrome blue black B, D & C green no. 2, Spirit soluble fast RR, Spirit soluble fast red 3B, D & C red no. 22, Nitro red, Congo red, Brilliant cresyl blue ALD, Arsenazo 1, Basic red 29, Bismarck brown R, Methylene violet, Methylene violet 3RAX, Mordant brown 1, Reactive black 5, Mordant brown 48, Acid brown AX987, Acid violet AX990, Basic red 15, Mordant red 19, Bromopyrogallol red, and combinations thereof.

Preferably, the colorant is selected from the group consisting of Ethyl violet, New fuchsin, Toluidine blue O, Luxol brilliant green BL, Disperse blue 1, Brilliant blue R, Quinea green B, Thionin, Meldolas blue, Methylene green, Lissamine green B, Alkali blue 6B, Brilliant green, Spirit soluble HLK BASF, Victoria green S extra, Acid violet 17, Eriochrome black T, Eriochrome blue black B, D & C green no. 2, Spirit soluble fast RR, Spirit soluble fast red 3B, D & C red no. 22, Nitro red, Congo red, Brilliant cresyl blue ALD, Arsenazo 1, Basic red 29, Bismarck brown R, Methylene violet, Methylene violet 3RAX, Mordant brown 1, Reactive black 5, Mordant brown 48, Acid brown AX987, Acid violet AX990, Mordant red 19, Bromopyrogallol red, and combinations thereof.

In a preferred embodiment the present invention provides a hydrogen peroxide indicator that includes a substrate and an indicator composition disposed thereon, wherein the indicator composition includes a binder, at least one colorant selected from the group consisting of Malachite green oxalate, Crystal violet, Methyl violet 2B, Ethyl violet, New fuchsin, Victoria blue B, Victoria pure blue BO, Toluidine blue O, Luxol brilliant green BL, Disperse blue 1, Brilliant blue R, Victoria blue R, Quinea green B, Thionin, Meldolas blue, Methylene green, Lissamine green B, Alkali blue 6B, Brilliant green, Spirit soluble HLK BASF, Victoria green S extra, Acid violet 17, Eriochrome black T, Eriochrome blue black B, D & C green no. 2, Spirit soluble fast RR, Spirit soluble fast red 3B, D & C red no. 22, Nitro red, Congo red, Brilliant cresyl blue ALD, Arsenazo 1, Basic red 29, Bismarck brown R, Methylene violet, Methylene violet 3RAX, Mordant brown 1, Reactive black 5, Mordant brown 48, Acid brown AX987, Acid violet AX990, Basic red 15, Mordant red 19, Bromopyrogallol red, and combinations thereof, and at least one colorant that does not change color upon contact with hydrogen peroxide vapor.

Methods of monitoring a hydrogen peroxide sterilization process is also provides. These methods include exposing an article to be sterilized and the hydrogen peroxide indicators as described herein to hydrogen peroxide vapor.

DETAILED DESCRIPTION OF PREFERRED EMBODIMENTS

The present invention provides a hydrogen peroxide indicator that includes a substrate on which is disposed an indicator composition that includes at least one of a select group of colorants. As a result of contact with hydrogen peroxide, the colorants change color, and even become colorless, thereby providing an indication of the presence of hydrogen peroxide.

In particular, the present invention is directed to a system for indicating exposure to a hydrogen peroxide vapor sterilization process. The indicator composition includes at least one component that is transformed (typically, chemically transformed) in the presence of vaporous hydrogen peroxide such that the color of the composition changes. The composition may include one or more components that change color upon contact with hydrogen peroxide, as well as other components that do not change color upon contact with hydrogen peroxide. For example, the composition preferably includes a polymeric binder to aid in applying the composition to a suitable substrate.

Indicators of the present invention are very useful in indicating when an article has been exposed to hydrogen peroxide in the vapor phase. Significantly, indicators of the present invention offer one a simple, yet effective means for indicating when a particular article has been subjected to sterilization using vaporous hydrogen peroxide.

Preferably, the indicator compositions of the present invention undergo a color change when exposed to an atmosphere above an aqueous solution containing 30 weight percent (wt-%) hydrogen peroxide at 50° C. within a period of at least about one hour and/or a color change when exposed to an atmosphere containing about 6 milligrams/liter (mg/l) to about 7 mg/l hydrogen peroxide (in an empty chamber, i.e., without articles to be sterilized) at a pressure of about $8 \times 10^2$ Pascals (Pa) to about $13.3 \times 10^2$ Pa and a temperature of about 45° C. to about 50° C. for a period of at least about 50 minutes, which are typical conditions within an empty commercial hydrogen peroxide plasma sterilizer. More preferably, for use in conventional sterilizers, the indicator compositions of the present invention undergo a color change when exposed to an atmosphere containing about 6 mg/l to about 7 mg/l hydrogen peroxide (in an empty chamber) at a pressure of about $8 \times 10^2$ Pa to about $13.3 \times 10^2$ Pa and a temperature of about 45° C. to about 50° C. for a period of at least about 50 minutes. As used herein, a color change includes becoming colorless.

Preferably, the indicator compositions do not significantly fade upon exposure to room lighting, e.g., fluorescent lighting. More preferably, the indicator compositions do not significantly fade, for example, upon exposure to sunlight through a window for one week or room lighting for two months.

Suitable colorants for use in the indicator compositions of the present invention include the following: Malachite green oxalate, Crystal violet, Methyl violet 2B, Ethyl violet, New fuchsin, Victoria blue B, Victoria pure blue BO, Toluidine blue O, Luxol brilliant green BL, Disperse blue 1, Brilliant blue R, Victoria blue R, Quinea green B, Thionin, Meldolas blue, Methylene green, Lissamine green B, Alkali blue 6B, Brilliant green, Spirit soluble HLK BASF, Victoria green S extra, Acid violet 17, Eriochrome black T, Eriochrome blue black B, D & C green no. 2, Spirit soluble fast RR, Spirit soluble fast red 3B, D & C red no. 22, Nitro red, Congo red, Brilliant cresyl blue ALD, Arsenazo 1, Basic red 29, Bismarck brown R, Methylene violet, Methylene violet 3RAX, Mordant, brown 1, Reactive black 5, Mordant brown 48, Acid brown AX987, Acid violet AX990, Basic red 15, Mordant red 19, and Bromopyrogallol red. Alternative names and Color Index Numbers for these colorants are listed in Tables 1 and 2 below. Various combinations of these colorants can be used in the indicator compositions of the present invention. Such mixtures or blends would increase the options available in color changes dramatically.

A preferred group of colorants include the following: Ethyl violet, New fuchsin, Toluidine blue O, Luxol brilliant green BL, Disperse blue 1, Brilliant blue R, Quinea green B, Thionin, Meldolas blue, Methylene green, Lissamine green B, Alkali blue 6B, Brilliant green, Spirit soluble HLK BASF, Victoria green S extra, Acid violet 17, Eriochrome black T, Eriochrome blue black B, D & C green no. 2, Spirit soluble fast RR, Spirit soluble fast red 3B, D & C red no. 22, Nitro red, Congo red, Brilliant cresyl blue ALD, Arsenazo 1, Basic red 29, Bismarck brown R, Methylene violet, Methylene violet 3RAX, Mordant brown 1, Reactive black 5, Mordant brown 48, Acid brown AX987, Acid violet AX990, Mordant red 19, Bromopyrogallol red, and combinations thereof.

Another preferred group of colorants include the following: Malachite green oxalate, Methyl violet 2B, New fuchsin, Toluidine blue O, Luxol brilliant green BL, Quinea green B, Thionin, Meldolas blue, Lissamine green B, Alkali blue 6B, Brilliant green, Victoria green S extra, Eriochrome blue black B, Congo red, Bismarck brown R, Methylene violet, Methylene violet 3RAX, Bromopyrogallol red, and combinations thereof.

Suitable colorants become colorless or change to a different color upon exposure to hydrogen peroxide vapor. Preferred are those colorants that show good contrast between the initial color and the color after exposure to hydrogen peroxide vapor. Examples include, Malachite green oxalate, Methyl violet 2B, New fuchsin, Quinea green B, Thionin, Meldolas blue, Lissamine green B, Alkali blue 6B, Congo red, Eriochrome blue black B, Bismarck brown R, Methylene violet 3RAX, and combinations thereof.

Another group of preferred colorants are those that become substantially colorless upon exposure to hydrogen peroxide vapors under conventional sterilization conditions (e.g., 6 mg/l to about 7 mg/l hydrogen peroxide in an empty chamber at a pressure of about $8 \times 10^2$ Pa to about $13.3 \times 10^2$ Pa and a temperature of about 45° C. to about 50° C. for a period of at least about 50 minutes) or to the more concentrated hydrogen peroxide vapors in a desiccator. Examples of such colorants include Toluidine blue O, Luxol brilliant green BL, Victoria green S extra, Methylene violet, Bromopyrogallol red, Brilliant green, and combinations thereof.

Such colorants that become substantially colorless after exposure to hydrogen peroxide can also be used in combination with other colorants (e.g., dyes or pigments) that do not change color in the presence of hydrogen peroxide to give a chemical indicator with a suitable contrasting color change. For example, Alkali blue 6B plus a red unreactive dye such as Quinacridone red 19 show a color change from blue (initial) to pink, or a mixture of Brilliant green and Auramine O show a color change from bright green (initial) to bright yellow. In addition to Quinacridone red 19 and Auramine O, other sterilant-immune colored components may include those examples indicated in Tables 3A and 3B below.

Preferably, at least one colorant is present in the indicator composition in an amount sufficient to cause a color change when the composition is exposed to an atmosphere above an aqueous solution containing 30% hydrogen peroxide at 50° C. within a period of at least about one hour and/or an amount sufficient to cause a color change when exposed to an atmosphere containing about 6 mg/l to about 7 mg/l hydrogen peroxide (in an empty chamber) at a pressure of about $8 \times 10^2$ Pa to about $13.3 \times 10^2$ Pa and a temperature of about 45° C. to about 50° C. for a period of at least about 50 minutes. Generally, the compositions contain about 0.1 wt-% to about 5.0 wt-%, based on the total weight of the composition, of a colorant that changes color upon exposure to hydrogen peroxide.

In effect, the colorant concentration should be such as to allow a clear visual indication of a color change. If at least one colorant that does not change color upon exposure to hydrogen peroxide is used in the indicator compositions of the present invention, it is present in an amount sufficient to provide the targeted color intensity, both prior to and subsequent to exposure to hydrogen peroxide vapor. Generally, such compositions contain about 0.1 wt-% to about 5.0 wt-%, based on the total weight of the composition, of a colorant that does not change color upon exposure to hydrogen peroxide.

The indicating composition is generally formulated in the form of a dispersion or solution in water or an organic solvent (preferably, an organic solvent). The composition includes at least one colorant as described above as well as an organic binder. A wide variety of suitable binders can be used. Examples include synthetic or natural polymers or resins. Suitable binders are those that do not interfere with the function of the indicator composition. Examples include cellulose acetate butyrate, shellac, ethyl cellulose, methyl cellulose, acrylic resins, etc. A sufficient amount of binder is included in the compositions to provide adequate binding of the composition to a substrate on which it is disposed, while providing the desired rate of color change. Generally, the compositions contain about 20 wt-% to about 40 wt-% of a polymer binder, based on the total weight of the composition.

Indicator compositions of the present invention can also include other resins that do not necessarily function as a binder. For example, the compositions can include a resin that functions as a dispersing agent, such as Rhoplex I-545, a water based acrylic polymer, available from Rohm and Haas Corp., Philadelphia, Pa., that assists in dispersing the ingredients of the composition in the solvent used in application of the composition to a substrate. Indicator compositions of the present invention can also include opacifying agents such as titanium dioxide, surfactants, plasticizers, antifoam agents, and the like. For certain embodiments, a basic material such as an organic amine (e.g., triethanolamine) can be used to enhance sensitivity of the colorant to the low concentration of hydrogen peroxide in a conventional sterilizer. Typically, such additives are used in no more than about 5 wt-% based on the total weight of the indicator composition.

The compositions are typically applied to a substrate out of a solvent as discussed above. Suitable solvents include water and organic solvents such as ketones, esters, alcohols, and the like. Examples of suitable solvents include methyl ethyl ketone, n-propyl acetate, and isopropanol. The solvent is typically used in an amount of about up to about 15 wt-%, based on the total weight of the composition. The indicator composition can be applied to the substrate by a wide variety of techniques, including, for example, printing or coating by flexographic, gravure, screen, or die processes.

The substrate on which the indicator composition is disposed can be any of a wide variety. Typically, suitable substrates include polymeric materials, which may be pigmented or colorless, such as polyester, polyethylene, or polystyrene films, paper, and the like. Preferably, it is a Melinex™ polyester film from E. I. du Pont de Nemours and Company, Wilmington, Del. The substrate may be in the form of a strip of material (e.g., a strip of material having the dimensions 2 cms by 13 cm). Optionally, the composition can be coated as a stripe over the length of the substrate strip. The substrate may also have an adhesive on the surface opposite that on which the indicator composition is disposed. In this way, the indicator may be used as a tape or label for attachment to the article to be sterilized The vapor sterilization procedure used is conventional, and is disclosed in, for example U.S. Pat. Nos. 4,756,882, 4,643,876, 4,956,145, and 5,445,792, for example. Preferably, it is a plasma-based sterilization system.

In general, the article to be sterilized is placed in a sterilization chamber, and a dose of hydrogen peroxide, which generally comes pre-measured, is delivered to the chamber. Vapor is generated and allowed to fill the container for an appropriate length of time after which the sterilization is complete. The equipment and the entire procedure is generally controlled electronically. When sterilizing medical instruments, one cycle is often sufficient. The medical instruments are often packaged, with the entire package being placed into the sterilizing compartment. The package allows the hydrogen peroxide to penetrate and effect sterilization of the instruments, while subsequently protecting the instruments from contamination in air. The temperatures used in the process of the present invention are all generally less than 65° C.

The invention will be illustrated in greater detail by the following specific examples. It is understood that these examples are given by way of illustration and are not meant to limit the disclosure or the claims to follow. All percentages in the examples, and elsewhere in the specification, are by weight unless otherwise specified.

EXAMPLES

Example 1

Preparation of Indicator Compositions

Indicator compositions were prepared by mixing 70 grams of a shellac binder solution containing 60% weight percent of shellac in isopropanol (commercially available as 5 pound refined shellac in 99 percent isopropanol form Mantrose, Bradshaw and Zinsser Group, Westport, Conn.), 17.5 grams of dispersing resin (commercially available as Rhoplex I-545 from Rohm & Haas Corp., Philadelphia, Pa.), in 15 grams of isopropanol, with approximately 0.1 gram or a sufficient amount of colorant (0.1 wt-% to 5 wt-%) to give a good color of the colorants listed in Table 1. The indicator compositions were mixed in glass jars containing marbles. The glass jars were rolled for three hours on a roller mill.

Coating of Indicator Compositions

An indicator composition was coated on a plastic backing (commercially available as "3M Printable Polyester Film Label Stock" from Minnesota Mining and Manufacturing Co., St. Paul, Minn.) using a number 16 Meyer bar (commercially available from R. D. Specialties, Webster, N.Y.). The coated ink was dried at 50° C. in an oven (commercially available as "Despatch Style V 29" from Despatch Oven Co., Minneapolis, Minn.) for 2 minutes. The coated film was cut using scissors to obtain indicators of approximately 2 cm by 13 cm.

Test Methods

One indicator composition was placed on an instrument tray lid and exposed to a full cycle of a hydrogen peroxide plasma sterilization procedure at 45-55° C. in a STERRAD™ 100SI GMP Sterilizer, obtained from Advanced Sterilization Products Co., Irvine, Calif. During the sterilization procedure a vacuum was drawn in the sterilization chamber for 5-6 minutes until the pressure was reduced to 40.0 Pa. A 1.8 ml aliquot of an aqueous solution of 58-60 percent hydrogen peroxide was then injected into the empty sterilization chamber over a period of about 6 minutes, yielding an empty chamber concentration of 6-7 mg/liter hydrogen peroxide. Hydrogen peroxide vapor was allowed to diffuse throughout the chamber for 44 minutes at $8 \times 10^2$ to $13.3 \times 10^2$ Pa. A vacuum was then drawn, reducing the pressure to 66.7 Pa and removing all detectable hydrogen peroxide vapor from the chamber. A plasma phase was then generated in the chamber by emitting an RF power source at 400 watts and 13.56 MHz for about 15-16 minutes at 66.7 Pa, after which the chamber was vented for 3-4 minutes until atmospheric pressure was reached in the chamber. After exposure to the sterilization procedure the indicators were removed from the tray lid and examined for color change. The results for each indicator composition are described in Table 1.

Some of the colorants were either the same color as they were initially or only slightly lighter, so another set of indicators were exposed to a higher concentration of hydrogen peroxide to determine if changing concentration would effect the results. A set of indicators were taped to a roll of film which was placed in a vented desiccator containing 80 ml of 30 weight percent (wt-%) hydrogen peroxide. The desiccator was placed in an oven (commercially available as "Despatch Style V 29" from Despatch Oven Co.) at 50° C. for one hour. The indicators were removed from the desiccator and examined for color change. The results for each indicator composition are also described in Table 1.

TABLE 1

Indicator Compositions

| Run No. | Colorant | Colorant Class | Color Index No. | Initial Color | Color Change when in Sterilizer | Color Change When in Desiccator (30% $H_2O_2$) |
|---|---|---|---|---|---|---|
| 1 | [1]Malachite green oxalate (Basic green 4) | Methane | 4200 | Blue/green | Pale green | Pale green |
| 2 | [1]Crystal violet (Gentian violet or Hexamethyl-pararosaniline chloride | Methane | 42555 | Very Dark Blue | Slightly Lighter | Lighter |
| 3 | [1]Methyl violet 2B (Basic violet 1) | Methane | 42535 | Fuchsia | Lighter | Light lavender |
| 4 | [1]Ethyl violet (Basic violet 4) | Methane | 42600 | Blue | No Change | Lighter |
| 5 | [1]New fuchsin (Basic violet 2 or Magenta III) | Anthraquinone | 42520 | Purple | Slightly lighter | Light pink |
| 6 | [1]Victoria blue B (Basic blue 26) | Methane | 44045 | Royal blue | Lighter | Lighter |
| 7 | [1]Victoria pure blue BO (Basic blue 7) | Methane | 42595 | Blue | Slightly Lighter | Lighter |
| 8 | [1]Toluidine blue O (BasicbBlue 17 or Tolonium chloride) | Thiazine | 52040 | Pale blue | No Change | Colorless |
| 9 | [1]Luxol brilliant green BL (Solvent green 11) | Methane | None | Blue/green | Pale green | Almost Colorless |
| 10 | [1]Disperse blue 1 (Solvent blue 18 or Celliton blue extra) | Anthraquinone | 46500 | Royal Blue | More gray | Dark gray blue |
| 11 | [1]Brilliant blue R (Acid blue 83 or Coomassie brilliant blue R) | Methane | 42660 | Blue | No Change | Lighter |
| 12 | [1]Victoria blue R (Basic blue 11) | Methane | 44040 | Royal blue | Slightly Lighter | Lighter |
| 13 | [1]Quinea green B (Acid green 3) | Methane | 42085 | Green | Pale green | Very pale green |
| 14 | [1]Thionin (Lauth's violet) | Thiazine | 52000 | Blue | No Change | Light gray |
| 15 | [1]Meldolas blue | Oxazine | 51175 | Dark lilac | Slightly Lighter | Pale beige |
| 16 | [1]Methylene green | Thiazine | 52020 | Light blue | None | Very Pale blue |
| 17 | [1]Lissamine green B (Acid Green 50 or Wool Green S) | Methane | 44090 | Blue (teal) | Slightly Lighter | Pale blue |
| 18 | [2]Alkali blue 6B (Acid Blue 119) | Methane | 42765 | Blue | Light grey blue | Light blue |
| 19 | [1]Brilliant Green (Basic Green 1) | Methane | 42040 | Green | Pale green | Colorless |

[1]Commercially available from Sigma-Aldrich Fine Chemicals, St. Louis, MO.
[2]Commercially available from ICN Biomedicals, Costa Mesa, CA.

Colorants that showed good contrast between the initial color and the color after exposure to hydrogen peroxide vapor are Malachite green oxalate, Methyl violet 2B, New fuchsin, Quinea green B, Thionin, Meldolas blue, Lissamine green B, and Alkali blue 6B.

Another set of preferred colorants for chemical indicators become colorless after exposure in the STERRAD™ Sterilizer or to the more concentrated hydrogen peroxide in a desiccator. Examples of these colorants include Toluidine blue O, Luxol brilliant green BL, and Brilliant green.

Example 2

Preparation of Indicator Compositions for Screening

A cellulose acetate butyrate binder was prepared by dissolving 15 grams of the cellulose acetate butyrate grade 553-0.4 resin (commercially available from Eastman Chemical Company, Kingsport, Tenn.) in 100 milliliters of methyl ethyl ketone. Indicator compositions were prepared by dissolving a sufficient amount (approximately 0.1 gram or more 0.1 wt-% to 5 wt-% of the colorants listed in Table 2 to give a good color in 15 milliliters of the binder.

The resulting indicator composition was coated as described for Example 1. Each indicator composition was exposed to a full cycle of a hydrogen peroxide plasma sterilization procedure in a STERRAD™ 100SI GMP Sterilizer as described in Example 1. The results for each indicator composition are described in Table 2.

As in Example 1 some of the colorants were either the same color as they were initially or only slightly lighter, so another set of indicators were exposed to a higher concentration of hydrogen peroxide to determine if changing concentration would effect the results. The results for each indicator composition are also described in Table 2.

TABLE 2

Indicator Compositions

| Run No. | Colorant | Colorant Class | Color Index No. | Initial Color | Color Change When in Sterilizer | Color Change when in Desiccator (30% $H_2O_2$) |
| --- | --- | --- | --- | --- | --- | --- |
| 20 | Spirit soluble HLK BASF | | | Green | No Change | Slightly Lighter |
| 21 | Victoria green S extra | | | Dark green | Almost Colorless | Very Pale green |
| 22 | [1]Acid violet 17 | Methane | 42650 | Purple | No Change | Lighter |
| 23 | [1]Eriochrome black T | Monazo | 14645 | D Brown | Slightly Lighter | None |
| 24 | [1]Eriochrome blue black B | Monazo | 14640 | Dark lilac | Lighter | Very Pale beige |
| 25 | D & C green no. 2 | | | Green/blue | Pale green | Pale green |
| 26 | Spirit soluble fast RR | | | Purple | Slightly Lighter | No Change |
| 27 | Spirit soluble fast red 3B | | | Fuchsia | Slightly Lighter | Lighter |
| 28 | D & C red no. 22 | | | Pink | No Change | Slightly Lighter |
| 29 | [1]Nitro red | Monazo | None | Lilac | Lighter | Lighter |
| 30 | [1]Congo red | Diazo | 22120 | Light red | Darker | Blue orange |
| 31 | [1]Brilliant cresyl blue ALD | Oxazine | | Light blue | No Change | Lighter |
| 32 | [1]Arsenazo 1 | Monazo | None | Very pale pink | No Change | Lighter |
| 33 | [1]Basic red 29 | Monazo | 11460 | Dark bold pink | No Change | Lighter |
| 34 | [1]Bismarck brown R | Diazo | 21010 | Brown/gold | No Change | Significantly Lighter |
| 35 | Methylene violet | | | Light purple | Darker | Colorless |
| 36 | [1]Methylene violet 3RAX | Diazine | 50206 | Fuchsia | No Change | Light pink |
| 37 | [1]Mordant brown 1 | Diazo | 20110 | Brown | Lighter | None |
| 38 | [1]Reactive black 5 | Diazo | 20505 | Very pale lilac | No Change | Light gray blue |
| 39 | [1]Mordant brown 48 | Monoazo | 11300 | Red/brown | Slightly Lighter | Significantly Lighter |
| 40 | [2]Acid brown AX987 | | | Lilac | Light blue | Light blue |
| 41 | [2]Acid violet AX990 | | 41001 | Dark lavender | Blue | Blue |
| 42 | [2]Basic red 15 | | | Red/pink | Lighter | Pale pink |
| 43 | Mordant red 19 | | | Beige | Lighter | Lighter |
| 44 | [1]Bromopyrogallol red | Methane | None | Lilac | Pale beige | Colorless |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.

Colorants that showed good contrast between the initial color and the color after exposure to hydrogen peroxide vapor are Eriochrome blue black B, Congo red, Bismarck brown R, and Methylene violet 3RAX.

Another set of preferred colorants for chemical indicators become colorless after exposure in the STERRAD™ Sterilizer or to the more concentrated hydrogen peroxide in a desiccator. Examples of these colorants include Victoria green S extra, Methylene violet, and Bromopyrogallol red.

Comparative Examples

The colorants listed in Table 3A were used to make chemical indicators as described in Example 1. While the colorants listed in Table 3B were used to make chemical indicators as described in Example 2. Each indicator composition was exposed to a full cycle of a hydrogen peroxide plasma sterilization procedure in a STERRAD™ 100SI GMP Sterilizer as described in Example 1. The results for each indicator composition are described in Table 3A or 3B.

As in Example 1, some of the colorants were either the same color as they were initially or only slightly lighter. Thus, another set of indicators were exposed to a higher concentration of hydrogen peroxide to determine if changing concentration would effect the results. The results for each indicator composition are also described in Table 3A or 3B.

TABLE 3A

Colorants for Indicator Compositions

| Run No. | Colorant | Colorant Class | Color Index No. | Initial Color | Color Change in Sterilizer | Color Change in Desiccator (30% $H_2O_2$) |
|---|---|---|---|---|---|---|
| 1 | [1]Brilliant blue G (Acid Blue 90 or Coomassie Brilliant Blue G 250) | Methane | 42655 | Blue | No Change | No Change |
| 2 | [1]Acid black 24 | Diazo | 26370 | Grey | No Change | No Change |
| 3 | [2]Patent blue violet | Methane |  | Blue | No Change | No Change |
| 4 | [1]Disperse red 13 (Celliton Scarlet B) | Monoazo | 11115 | Purple | No Change | No Change |
| 5 | [1]Sudan black B | Diazo | 26150 | Blue/Black | No Change | No Change |
| 6 | [1]Janus green B | Monoazo | 11050 | Blue | No Change | No Change |
| 7 | [1]Acridine orange base (Solvent Orange 15) | Acridine | 46005 | Orange | No Change | No Change |
| 8 | [1]Fast green FCF (Food Green 3) | Methane | 42053 | Blue (teal) | No Change | No Change |
| 9 | [1]Patent blue VF (Acid Blue 1) | Methane | 42045 | Dark blue |  | No Change |

[1]Commercially available from Sigma-Aldrich Fine Chemicals, St. Louis, MO.
[2]Commercially available from ICN Biomedicals, Costa Mesa, CA.

TABLE 3B

Colorants for Indicator Compositions

| Run No. | Colorant | Colorant Class | Color Index No. | Initial Color | Color Change in Sterilizer | Color Change in Desiccator (30% $H_2O_2$) |
|---|---|---|---|---|---|---|
| 10 | [1]Acid red 97 | Diazo | 22890 | Red/orange | No Change | No Change |
| 11 | [1]Sulforhodamine B | Xanthene | 45100 | Dark pink | No Change | No Change |
| 12 | Xylenol orange sodium salt |  |  | Light pink | No Change | No Change |
| 13 | Azure B |  |  | Pale blue | No Change | No Change |
| 14 | Spirit soluble fast yellow G |  |  | Yellow | No Change | No Change |
| 15 | [3]Keystone soap fluoro green |  |  | Blue/green | No Change | No Change |
| 16 | [3]Calco oil blue N |  | None | Blue | No Change | No Change |
| 17 | [3]Oil blue A |  |  | Light blue | No Change | No Change |
| 18 | [3]Calco oil green |  |  | Green | No Change | No Change |
| 19 | [3]D & C red no. 33 | Monoazo | 17200 | Pink | No Change | No Change |
| 20 | [3]D & C green no. 5 | Anthraquinone | 61570 | Pale blue | No Change | No Change |
| 21 | Bordeaux R |  |  | Light pink | No Change | No Change |
| 22 | [1]Xylenol cyanole FF | Methane | 42135 | Blue | No Change | No Change |
| 23 | Crystal scarlet |  |  | Light pink | No Change | No Change |
| 24 | Basic blue 41 |  |  | Dark blue | No Change | No Change |
| 25 | [1]Evans blue | Diazo | 23860 | Blue | No Change | No Change |
| 26 | [1]Chicago sky blue 6B | Diazo | 24410 | Blue | No Change | No Change |
| 27 | [1]Acid blue 113 | Diazo | 26360 | Blue | No Change | No Change |
| 28 | [1]Acid blue 120 | Diazo | 26400 | Grey/blue | No Change |  |
| 29 | Acid red 88 |  |  | Dark pink | No Change | No Change |
| 30 | Acid red 151 |  |  | Red/pink | No Change | No Change |
| 31 | [1]Acid violet 5 | Monoazo | 18125 | Dark lavender | No Change | No Change |
| 32 | [1]Disperse red 1 | Monoazo | 11110 | Red/orange | No Change | No Change |
| 33 | Direct red 81 |  |  | Pale pink | No Change | No Change |
| 34 | [1]Disperse red 19 | Monoazo | 11130 | Dark orange | No Change | No Change |
| 35 | [1]Sudan red 7B | Diazo | 26050 | Dark pink | No Change | No Change |
| 36 | [2]Basic red 73 |  |  | Light red | No Change | No Change |
| 37 | [3]Acid green AX986 |  |  | Lime green | No Change | No Change |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.

Example 4

A preferred composition was prepared as described in Example 1 using the components and the amounts given in Table 4. The resulting indicator composition was coated as described for Example 1. Each indicator composition was exposed to a full cycle of a hydrogen peroxide plasma sterilization procedure in a STERRAD™ 100SI GMP Sterilizer as described in Example 1.

TABLE 4

| Indicator Composition | Weight Percent |
|---|---|
| Shellac Binder | 70.2 |
| Rhoplex I-545 Water based Acrylic Polymer Resin | 23.0 |
| Alkali Blue 6B | 00.6 |
| Quinacridone red 19 available as Sunfast Red 19 | 00.3 |
| Triethanolamine | 02.0 |
| Isopropanol | 03.9 |

Colorants that become colorless after exposure in the STERRAD™ Sterilizer or to the more concentrated hydrogen peroxide in a desiccator can be used in combination with dyes or pigments which are stable to hydrogen peroxide to give a chemical indicator with a suitable contrasting color change. For example, Alkali blue 6B plus a red unreactive dye such as Quinacridone red 19 (commercially available as Sunfast Red 19 from Sun Chemical Corporation, Cincinnati, Ohio) showed a color change from blue (initial) to pink after exposure in the STERRAD™ Sterilizer. Another example was made by combining Brilliant green and Auramine O (commercially available from Sigma Aldrich Fine Chemicals, St. Louis, Mo.) which showed a color change from bright green (initial) to bright yellow after exposure in the STERRAD™ Sterilizer.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A hydrogen peroxide sterilization indicator comprising a substrate and an indicator composition disposed thereon, wherein the indicator composition comprises:
    at least one first colorant selected from the group consisting of Ethyl violet, New fuchsin, Victoria blue B, Victoria pure blue BO, Toluidine blue O, Luxol brilliant green BL, Disperse blue 1, Brilliant blue R, Victoria blue R, Quinea green B, Meldolas blue, Lissamine green B, Alkali blue 6B, Brilliant green, Spirit soluble HLK BASF, Victoria green S extra, Acid violet 17, Eriochrome black T, Eriochrome blue black B, D & C green no. 2, Spirit soluble fast RR, Spirit soluble fast red 3B, D & C red no. 22, Nitro red, Congo red, Brilliant cresyl blue ALD, Arsenazo 1, Basic red 29, Bismarck brown R, Methylene violet, Methylene violet 3RAX, Mordant brown 1, Reactive black 5, Mordant brown 48, Acid brown AX987, Acid violet AX990, Basic red 15, Mordant red 19, Bromopyrogallol red, and combinations thereof; and
    at least one second colorant that does not change color upon contact with hydrogen peroxide vapor, wherein the second colorant that does not change color upon contact with hydrogen peroxide vapor is selected from the group consisting off Quinacridone red 19, Auramine O, Brilliant blue G, Acid black 24, Patent blue violet, Disperse red 13, Sudan black B, Janus green B, Acridine orange base, Fast green FCF, Patent blue VF, Acid red 97, Sulforhodamine B, Xylenol orange sodium salt, Azure B, Spirit soluble fast yellow G, Keystone soap fluoro green, Calco oil blue N, Oil blue A, Calco oil green, D & C red no. 33, D & C green no. 5, Bordeaux R, Xylenol cyanole FF, Crystal scarlet, Basic blue 41, Evans blue, Chicago sky blue 6B, Acid blue 113, Acid blue 120, Acid red 88, Acid red 151, Acid violet 5, Disperse red 1, Direct red 81, Disperse red 19, Sudan red 7B, Basic red 73, Acid green AX986, and combinations thereof;
    and further wherein the composition changes color in the presence of hydrogen peroxide, and wherein the indicator composition comprises Alkali blue 6B as the at least one first colorant and Quinacridone red 19 as the at least one second colorant.

2. The hydrogen peroxide sterilization indicator of claim 1, wherein the substrate is a polyester film.

* * * * *

UNITED STATES PATENT AND TRADEMARK OFFICE
CERTIFICATE OF CORRECTION

PATENT NO. : 7,481,975 B2  
APPLICATION NO. : 10/890612  
DATED : January 27, 2009  
INVENTOR(S) : David M. Read It is certified that error appears in the above-identified patent and that said Letters Patent is hereby corrected as shown below:

Page 2, Column 1 (Other Publications)  
Lines 1-2, Delete "Classifaction,"" and insert -- Classification," --, therefor.

Column 1  
Line 8, Delete "Allowed" and insert -- Pat. No. 6,790,411 --.

Column 3  
Line 42, Delete "Mordant," and insert -- Mordant --, therefor.

Column 5  
Line 48, After "sterilized" insert -- . --.

Column 7-8 (Table 1)  
Line 13, After "chloride" insert -- ) --.  
Line 28, Delete "(BasicbBlue" and insert -- (Basic Blue --, therefor.

Column 9  
Line 61, After "55 wt-%" insert -- ) --.

Column 14  
Line 25, Delete "off" and insert -- of --.

Signed and Sealed this

Twenty-ninth Day of September, 2009

David J. Kappos  
*Director of the United States Patent and Trademark Office*